United States Patent
Masakov et al.

(10) Patent No.: US 6,572,558 B2
(45) Date of Patent: Jun. 3, 2003

(54) APPARATUS AND METHOD FOR NON-INVASIVE MEASUREMENT OF CURRENT FUNCTIONAL STATE AND ADAPTIVE RESPONSE IN HUMANS

(75) Inventors: Leonid Vasilyevich Masakov, Eugene, OR (US); Vladimir Borisovich Larionov, Eugene, OR (US)

(73) Assignee: OmegaWave, LLC, Sutherlin, OR (US)

(*) Notice: Subject to any disclaimer, the term of this patent is extended or adjusted under 35 U.S.C. 154(b) by 7 days.

(21) Appl. No.: 09/854,988

(22) Filed: May 13, 2001

(65) Prior Publication Data

US 2002/0045835 A1 Apr. 18, 2002

Related U.S. Application Data

(60) Provisional application No. 60/204,424, filed on May 13, 2000.

(51) Int. Cl.$^7$ ............................................. A61B 5/02
(52) U.S. Cl. ............ 600/483; 600/300; 600/301; 600/508; 600/544; 128/920
(58) Field of Search ................... 600/300, 301, 600/481, 483, 508, 509, 544, 545, 554, 555; 128/920, 923, 924, 925

(56) References Cited

U.S. PATENT DOCUMENTS 5,771,897 A * 6/1998 Zufrin ........................ 600/300
5,941,820 A * 8/1999 Zimmerman ................ 600/300

* cited by examiner

Primary Examiner—Max F. Hindenburg
Assistant Examiner—N. Natnithithadha
(74) Attorney, Agent, or Firm—Steven J. Adamson

(57) ABSTRACT

An apparatus and method for non-invasively assessing the functional state and state of homeostasis of a human. Specifically selected and designed tests provide efficient and comprehensive and/or targeted assessment, depending on which tests are selected. The tests preferably include heart rate variability, differential ECG, omega brain wave, jump and stimulus response tests. The non-invasive manner of data recording permits frequent testing which is critical in assessing adaptive response and other performance criteria. The sensors, interface/adapter and computing device are preferably lightweight to promote portability.

30 Claims, 7 Drawing Sheets

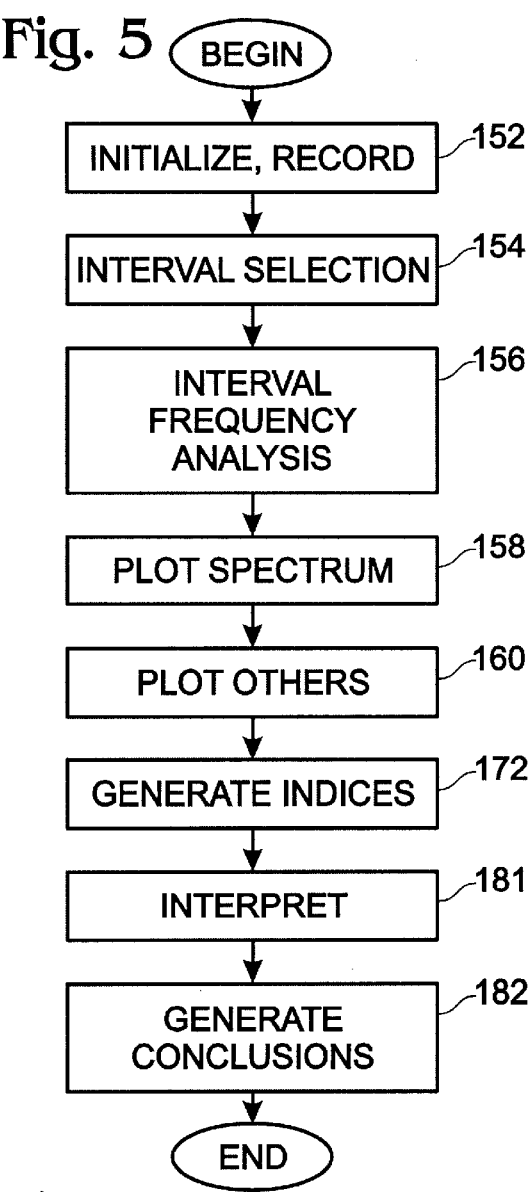
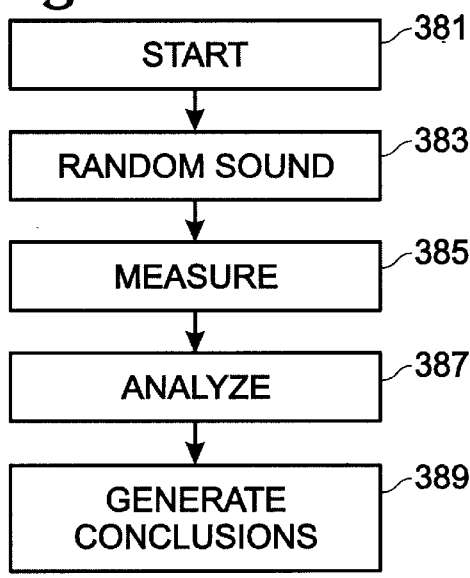
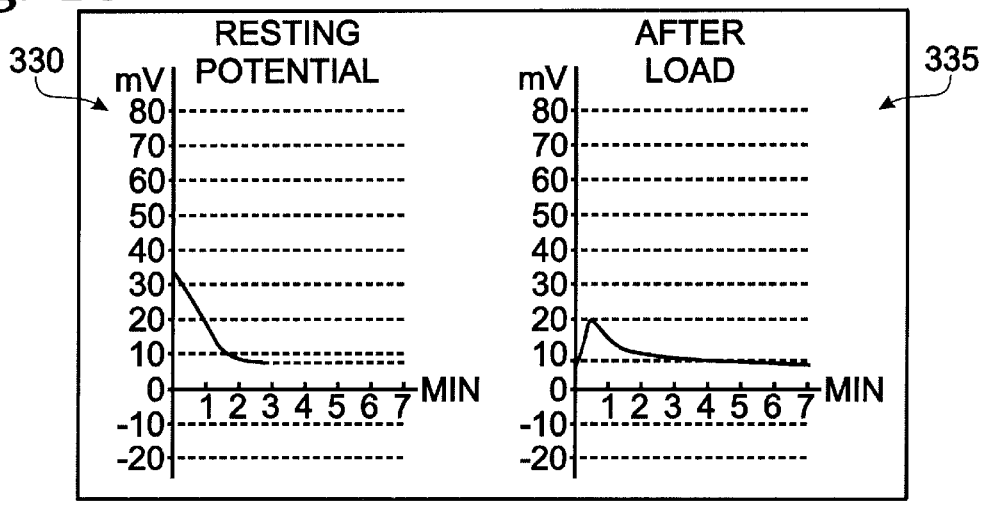

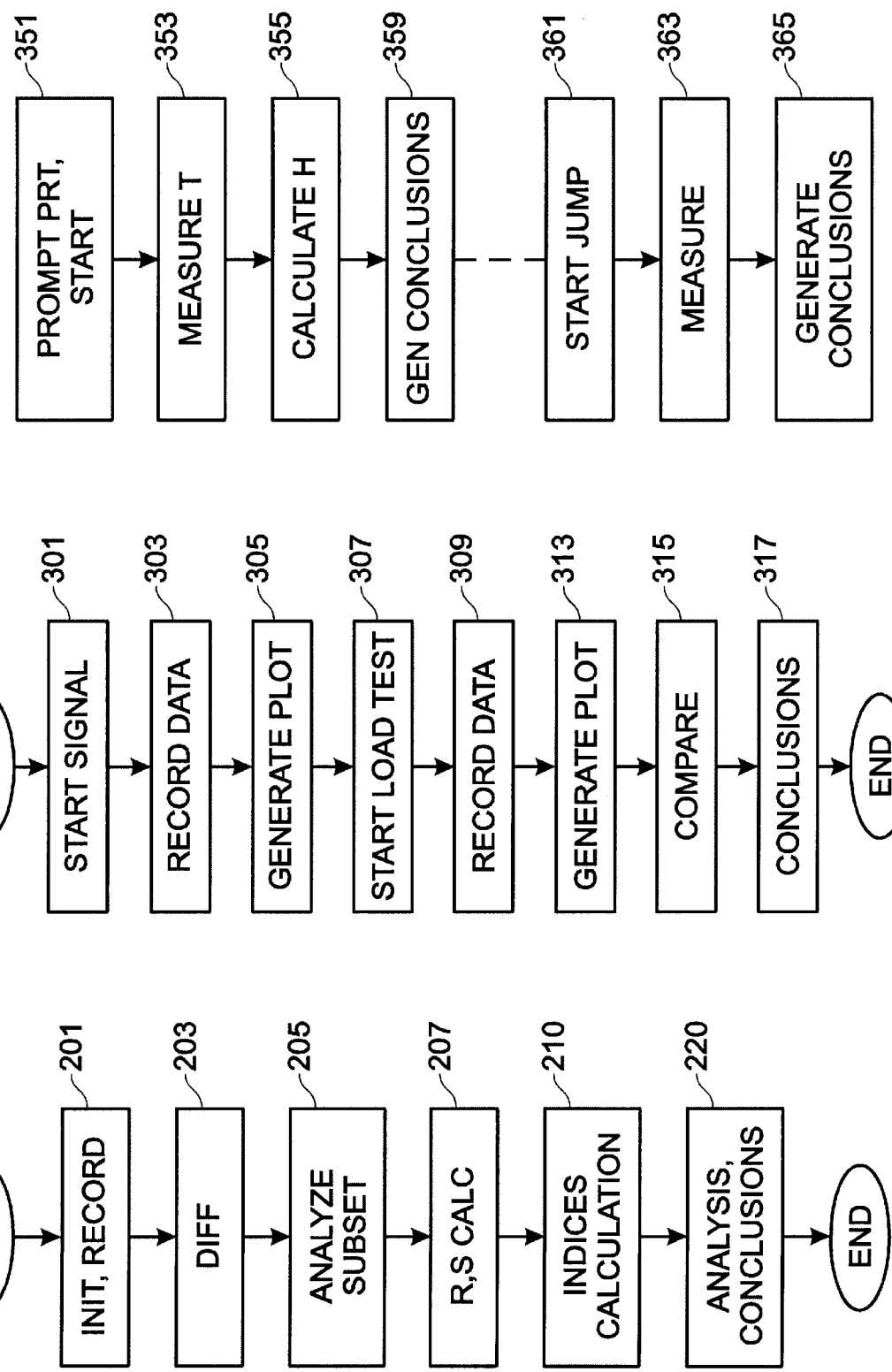

Fig. 8

| PARAMETER | VALUE | NORM | CURRENT FUNCTIONAL STATE OF ENERGY SUPPLY SYSTEM IS CHARACTERIZED BY: |
|---|---|---|---|
| AEROBIC POWER INDEX | 67 | 58-95 | SATISFACTORY FUNCTIONAL RESERVE; |
| AEROBIC EFFICIENCY INDEX | 70 | 60-90 | |
| ALACTATIAL QUANTITY INDEX | 15 | 11-25 | DECREASING OF THE SPEED OF THE RECOVERY PROCESSES; |
| LACTATIAL QUANTITY INDEX | 15 | 12-20 | |
| ANAEROBIC POWER INDEX | 103 | 100-300 | MODERATE RESISTANCE TO HYPOXIA; |
| MAIN METHABOLIC POWER INDEX | 214 | 210-250 | |
| SYSTEM'S ADAPTION INDEX | 134 | 120-148 | GOOD AEROBIC RESERVES |
| HR AT MAXIMUM OXYGEN CONSUMPTION | 188 | 179-210 | |
| HR AT ANAEROBIC LEVEL | 169 | 150-180 | |

Fig. 11

| CHANGE OF THE Ω POTENTIAL AFTER A LOAD IN % OF THE BASE POTENTIAL | CHARACTERISTICS OF THE MECHANISMS OF REGULATION OF SYSTEMS (CORRESPONDING TO TIME ZONES) | | |
|---|---|---|---|
| | A | B | C |
| >25 | INSIGNIFICANT HYPERFUNCTION | SIGNIFICANT HYPERFUNCTION | INSIGNIFICANT HYPERFUNCTION |
| >50 | SIGNIFICANT HYPERFUNCTION | SIGNIFICANT HYPERFUNCTION | SIGNIFICANT HYPERFUNCTION |
| FROM 0 TO ±25 | NORM | INSIGNIFICANT HYPERFUNCTION | NORM |
| <25 | INSIGNIFICANT HYPOFUNCTION | NORM | INSIGNIFICANT HYPOFUNCTION |
| <50 | SIGNIFICANT HYPOFUNCTION | NORM | SIGNIFICANT HYPOFUNCTION |

Fig. 14

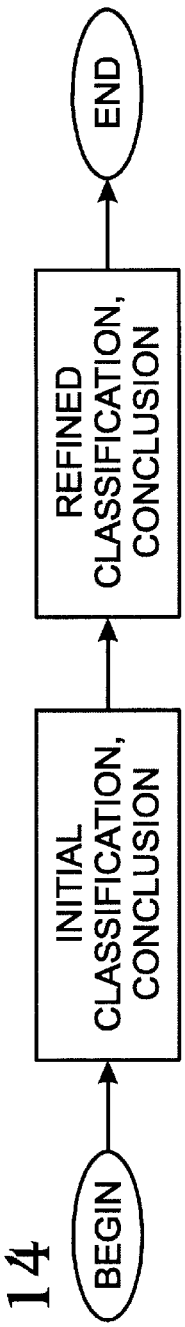

BEGIN → INITIAL CLASSIFICATION, CONCLUSION → REFINED CLASSIFICATION, CONCLUSION → END

APPARATUS AND METHOD FOR NON-INVASIVE MEASUREMENT OF CURRENT FUNCTIONAL STATE AND ADAPTIVE RESPONSE IN HUMANS

CROSS REFERENCE TO RELATED APPLICATIONS

This application claims the benefit of earlier filed U.S. provisional patent application No. 60/204,424, filed May 13, 2000, by the inventors listed above and entitled Apparatus and Method for Diagnosing Physical State and Potential.

FIELD OF THE INVENTION

The present invention relates to non-invasive and/or indirect determination of a person's current functional state and state of homeostasis. The present invention also monitors adaptive response to a stress.

BACKGROUND OF THE INVENTION

The human body is constantly being stressed (*The Stress of Life*, Hans Selye, M D, McGraw Hill, rev. ed., (1978)). Positive adaptation to stress can lead to an improved physical state (e.g., athletic training), while a breakdown in adaptation can result in the onset of significant medical conditions (e.g., heart attack, etc.).

Monitoring changes in a person's functional state and state of homeostasis provides an understanding of that person's adaptation to stress. In order to see changes in a person's functional state and state of homeostasis, testing must be done on a frequent basis and must include test of the major systems in the human body. These include the systems that regulate cardiac activity, energy metabolism, the central nervous system, the gas exchange and cardio-pulmonary (circulatory) system, the detoxification system and the homonal (adrenal) system.

Various invasive and non-invasive tests are known for assessing the functional state of a person. Invasive tests include blood tests and biopsies, etc., that damage tissue in carrying out the test. Disadvantages of invasive tests include pain, tissue damage, risk of infection and inability to perform the test with high frequency (due to the associated tissue damage). Invasive tests also tend to be relatively expensive and often require a visit to a medical facility (as opposed to home or field use).

Pseudo-invasive tests include tests that are not literally invasive, but which cannot be repeated with high regularity due to deleterious effects on the body. Examples include X-rays (excess radiation) and VO2 maximum treadmill tests which require a person to run to exhaustion (this may be difficult or impossible for person in a weakened physical state to perform regularly). With the exception of direct tissue damage, pseudo-invasive tests tend to suffer from the same disadvantages listed above for invasive tests.

In contrast to invasive tests, non-invasive tests tend to have much lower incidence of tissue damage or the like and, therefore, they can be practiced with higher frequency. Examples include temperature and blood pressure testing. While non-invasive tests are beneficial in that they can be practiced more regularly and tend to be less expensive, they are also disadvantageous in that they tend to provide a limited, direct measurement of a physical condition parameter. For example, a blood pressure reading simply states the current blood pressure, but does not provide information on what body system or systems are functioning improperly and causing the blood pressure to be high or low.

In order to better assess a person's health and adaptive response, it is desirable and part of the present invention to obtain and generate more information about that person's current functional state. This can be done in part by making indirect assessment of a person's health based on directly measured parameters. It can also be done by testing a greater number of body systems and/or strategically selecting or designing tests that provide comprehensive assessment data from a small number of tests.

While the present invention (as discussed in more detail below) provides a patentably distinct testing apparatus and method, prior art techniques for indirectly assessing functional state are known. For example, it is known to calculate VO2 maximum from heart rate response in a step test or from a differential ECG.

While some non-invasive, indirect tests and testing procedures are known in the art, prior teachings in this area are disadvantageous in that they fail to recognize that specific combinations of tests can provide more comprehensive, efficient and inexpensive assessment of current functional state and/or adaptive response. As a result, the prior art fails to address the problems discussed in the initial paragraphs above, amongst other problems.

A need thus exists for an apparatus and a method that provide a combination of non-invasive tests that more comprehensively, efficiently and inexpensively assess a person's current functional state and their state of homeostasis. A need also exists for an apparatus and a method that permit frequent testing due at least in part to non-invasive and non-stressful testing practices.

SUMMARY OF THE INVENTION

Accordingly, it is an object of the present invention to provide comprehensive, efficient and inexpensive assessment of a person's current functional state. This may include their adaptive response to a stress and/or potential for physical work.

It is another object of the present invention to provide this assessment in a non-invasive manner.

It is another object of the present invention to develop indirectly determined parameters or conclusions from non-invasively measured data.

It is another object of the present invention to provide or perform specific combinations of non-invasive tests to facilitate targeted assessment of functional state.

It is also an object of the present invention to provide this assessment in a manner that permits frequent testing.

These and related objects of the present invention are achieved by use of an apparatus and method of non-invasive measurement of current functional state and adaptive response in humans as described herein.

In one embodiment, the present invention includes a sensed data receiving circuit or logic and processing logic coupled thereto. The processing logic preferably conducts at least two body system functional state tests from the group of tests including: heart rate variability, differential ECG, brain wave, jump and stimulus response tests. The processing logic preferably processes received sensed data and generated signals representative of a textual conclusion of the functional state of a body system that corresponds to a given text.

In another embodiment, the present invention includes processing logic that monitors both cardiac activity and brain wave activity in assessing the functional state of one or more body systems.

In another embodiment, the present invention includes processing logic that uses rules-based analysis to interpret sensed data, and may further utilize the rules-bases analysis to generate textual or graphical conclusions of functional state.

Processing logic with the present invention may generate indices from sensed data and then interpret one or more indices to generate a particular conclusion regarding the functional state of a corresponding body system.

The present invention includes both apparatus and method embodiments of carrying out these, related and other features.

The attainment of the foregoing and related advantages and features of the invention should be more readily apparent to those skilled in the art, after review of the following more detailed description of the invention taken together with the drawings.

BRIEF DESCRIPTION OF THE DRAWINGS

FIG. 5 is a flow diagram of machine executable steps for a representative HRV test in accordance with the present invention.

FIG. 7 is a flow diagram of machine executable steps for a representative differential ECG test in accordance with the present invention.

FIG. 8 illustrates a display of data generated in the DECG test of FIG. 7 in accordance with the present invention.

FIG. 9 is a flow diagram of machine executable steps for a representative omega brain wave test in accordance with the present invention.

FIG. 10 is a display of data generated in the omega wave test of FIG. 9 in accordance with the present invention.

FIG. 11 is a diagram that illustrates an interpretation of differences between base and post-load omega potentials in accordance with the present invention.

FIG. 12 is a flow diagram of machine executable steps for a representative jump test in accordance with the present invention.

FIG. 13 is a flow diagram of machine executable steps for a representative stimulus response test in accordance with the present invention.

FIG. 14 is a flow diagram of rules-based analysis in accordance with the present invention.

DETAILED DESCRIPTION

Homeostasis is the tendency to maintain internal stability within an organism by coordinated responses of the organ systems that automatically compensate for external stresses. In the human body, the major organ or body systems include cardiac, metabolic, circulatory, detoxification, hormonal (adrenal), central nervous (CN) and neuromuscular systems. The present invention provides for a plurality of tests that monitor the organ or body systems. Tests within the present invention include, but are not limited to, heart rate variability (HRV), differential ECG (DECG), omega brain wave (OW), jump and stimulus response (SR) tests. The present invention assists in identifying which body systems are not functioning properly, i.e., affecting homeostasis, and how the body may be responding to a particular stress, e.g., exercise, dieting, illness, heart attach recovery, etc. Five preferred tests and the equipment for conducting those tests are now disclosed. While five tests are described in herein, the practice of at least a combination of any two or more of these tests is considered to be within the present invention.

Figure 1:
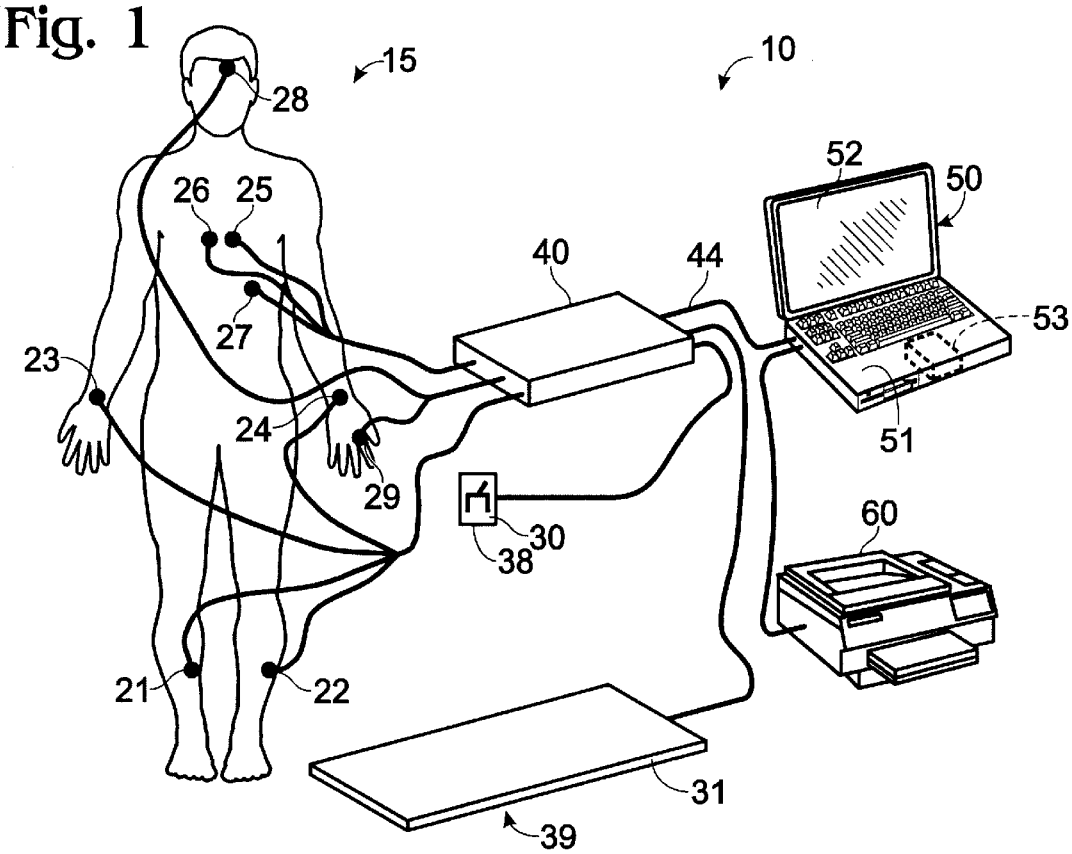
FIG. 1 is a diagrammatic representation of a non-invasive testing system in accordance with the present invention.

FIG. 1 is a diagrammatic representation of a non-invasive diagnostic testing system 10 in accordance with the present invention. FIG. 1 illustrates one embodiment of preferred components of the system and various electrode/sensor placements on the human body. Table I below provides a list of physical tests preferably conducted by the equipment of FIG. 1 and the corresponding body systems that are monitored by those tests.

TABLE I

| Body System Tests | |
|---|---|
| Tests | Body System Examined |
| 1. Heart Rate Variability | Cardio System |
| 2. Differential ECG | Metabolic |
| 3. Omega Wave | Circulation, Detox, Adrenal, CN |
| 4. Jump | Neuro-Muscular |
| 5. Stimulus Response | CN |

These five tests are preferred because they provide a relatively comprehensive assessment of functional state, by virtue of the various body systems that they measure/monitor. It should be recognized, however, that individual tests or combinations of tests (less than all), particularly when assessing a specific condition or response, may be performed as an alternative to conducting all tests. It should also be recognized that additional tests may be performed, e.g., a convention ECG, etc., and that the non-invasive tests taught herein may be used with or without invasive tests to determine the functional state of a person.

The non-invasive diagnostic system 10 includes a plurality of sensors 21–31 (sensors 30 and 31 are provided in the reaction button 38 and contact mat 39, respectively) for assessing the functional state of a person receiving a test (PRT) 15. These sensors are coupled to an interface device (ID) 40 that functions to channel signals through to a computing device (CD) 50 and to protect a person receiving a test (PRT) from electrical shock. ID 40 (which is discussed in more detail with reference to FIG. 2) preferably amplifies, filters and digitizes analog signals from the sensors.

CD 50 may be a conventional computer (laptop, personal or other) or another computing device (for example, that includes processing circuitry, memory, operator input control and a display element or access to same). In FIG. 1, CD 50 is illustrated as a personal computer 50 with a keyboard 51, a monitor 52 and processing logic 53. CD 50 may be coupled to a printer 60 to generate, for example, a printed copy of test results.

Figure 2:
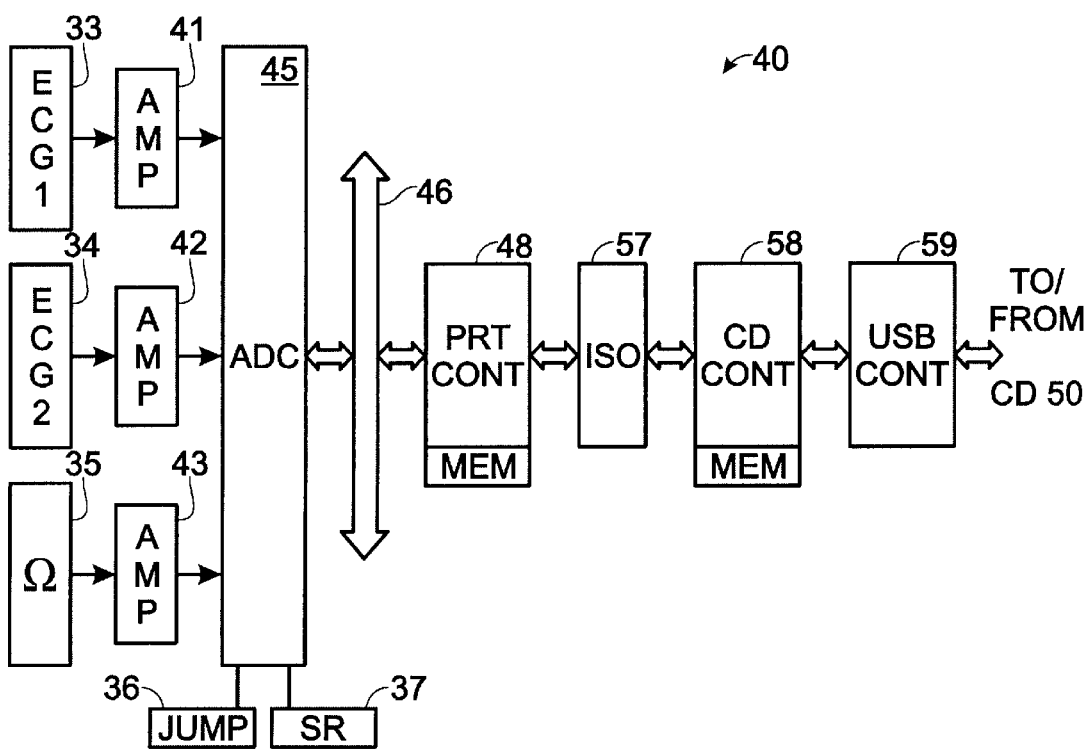
FIG. 2 is a schematic diagram of an interface device 40 in accordance with the present invention.

Referring to FIG. 2, a schematic diagram of an interface device 40 in accordance with the present invention is shown. ID 40 preferably includes a plurality of sensor ports: ECG1 (33) for HRV sensors 21–24, ECG2 (34) for additional DECG sensors 25–27, omega port (35) for the omega wave sensors 28–29, jump port (36) for the jump sensor 30 and stimulus response (SR) port (37) for the SR sensor 31. Amplifiers 41–43 provide amplification of ECG and omega wave signals. Data from each of the ports is preferably digitized by ADC 45 and propagated onto bus 46.

Data flow on and off of bus 46 is controlled in part by PRT-side microcontroller 48. A similar CD-side microcontroller 58 is also provided. These controllers 48, 58 are preferably separated by a galvanic isolator 57 which protects a PRT from electric shock due to CD-side malfunction. Sensed data is selectively propagated from bus 46 to CD 50. A USB controller or the like 59 controls propagation of sensed data to CD 50 (over cable 44) and receipt of signals from CD 50 such as initialization and port selection requests, etc.

Figure 3:
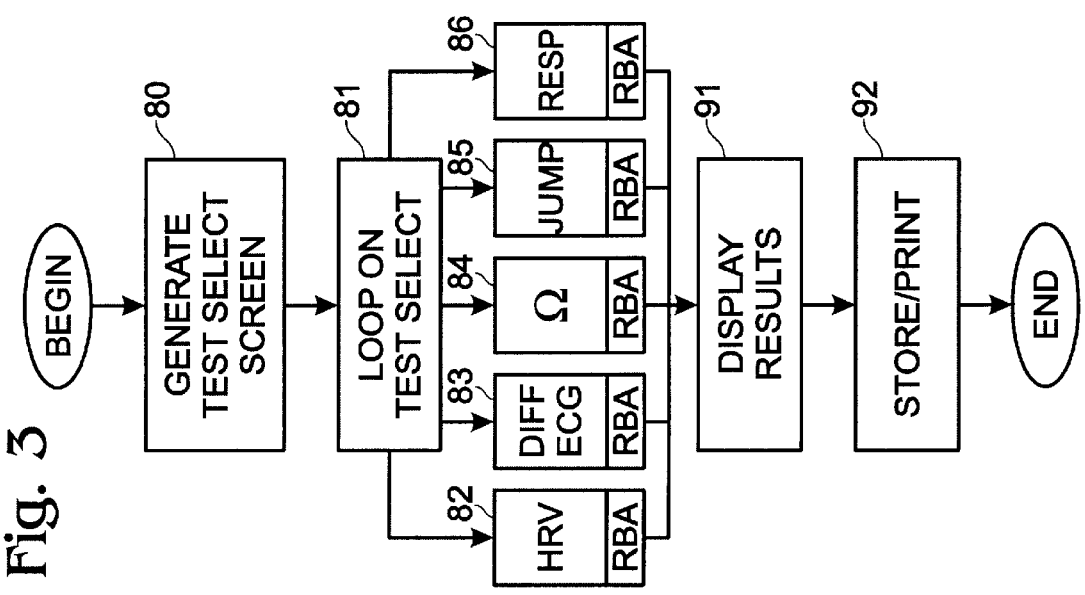
FIG. 3 is a diagram that provides a general overview of testing procedures in accordance with the present invention.

Referring to FIG. 3, a high level flow diagram of machine executable steps for performing a functional state assessment in accordance with the present invention is shown. In step 80, logic in CD 50 preferably generates a display on monitor 52 that permits a user to select the test or tests to be performed. Upon selection of a test, flow is routed to the code for executing the selected test (step 81). Blocks 82–86 represent logic for executing the tests of Table 1. Each of these tests in described in more detail below. The RBA block within blocks 82–86 represents the preferred rules-based analysis for determining textual conclusions of functional state. Step 91 represents code or logic for displaying test results (which may include calculated indices and textual conclusions) and step 92 represents print out or longer term storage of the test results.

Figure 4:
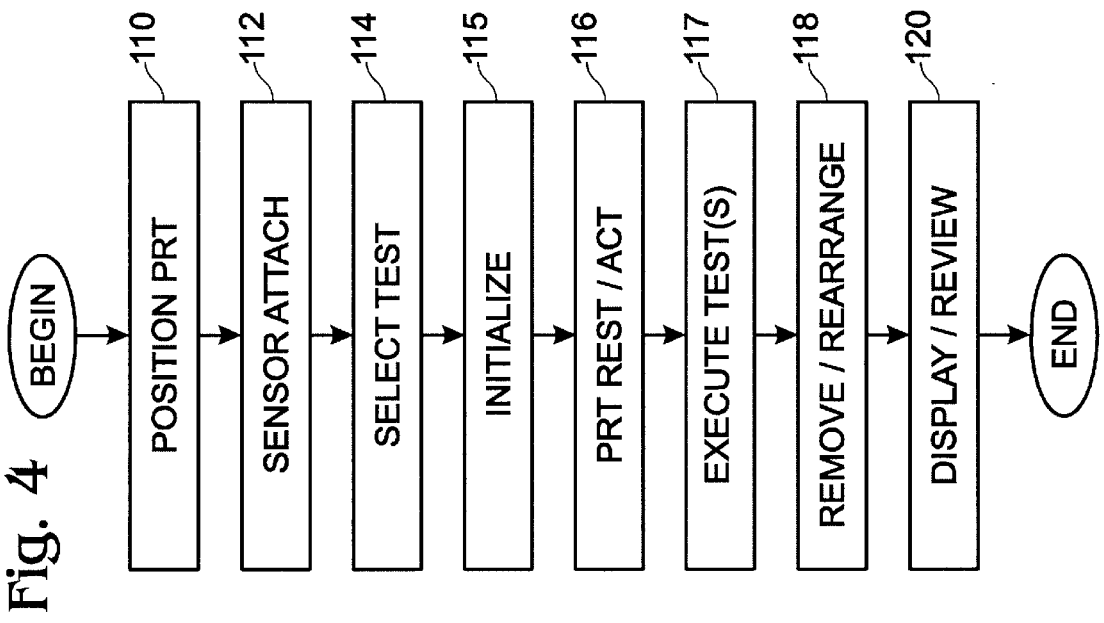
FIG. 4 is a diagram that generally illustrates the steps of conducting one or more body system tests in accordance with the present invention.

Referring to FIG. 4, a diagram that illustrates the steps of conducting one or more body system tests in accordance with the present invention is shown. In step 110, a person receiving a test (PRT) positions him or herself for sensor attachment. In step 112, the sensors are attached. In step 114, a user selects a desired test or tests from CD 50. Depending on the nature of the test(s) and the configuration of ID 40 (i.e., port arrangement, etc.), multiple tests may be conducted at the same time. In step 115, ID 40 is initialized for appropriate data sensing and data propagation by CD 50. In step 116, the PRT is instructed to attain or maintain a state of rest or to perform a certain action, e.g., jump (step 116). In step 117, the machine executable steps of the selected test(s) is/are carried out by CD 50. After test completion, the sensor electrodes are removed or rearranged (step 118) and the results are displayed for review (step 120). The results may be displayed on monitor 52 or printed via printer 60 or displayed by some other display mechanism. A description of machine executable steps of the test(s) selected in step 114 of FIG. 5 (or step 81 of FIG. 3) is now presented.

Heart Rate Variability (HRV) Test—Cardiac

The heart rate variability test (HRV) is designed to give an indication of the state of the biological systems that regulate cardiac activity. The cardiac system functions best when it is regulated by the autonomic circuit. When homeostasis is broken (unbalanced) higher levels of the central regulatory system dominate cardiac activity. These changes in regulation are reflected in the variability of the heart rhythm. Processing cardiac signals as discussed below permits quantitative and qualitative analysis of the functional state of cardiac activity.

The following is a representative HRV test. It should be recognized that other or related tests that differ from the specific protocol recited below are also within the present invention.

In general, an HRV test conducted via system 10 records sensor data, constructs charts or "grams" (i.e., scatter-grams, histograms, frequency spectrum-grams, etc.) that reflect the sensed data, calculates indices from the grams and data, and performs rules based analysis of the indices values to generate textual conclusions of the functional state of cardiac activity.

Figure 6:
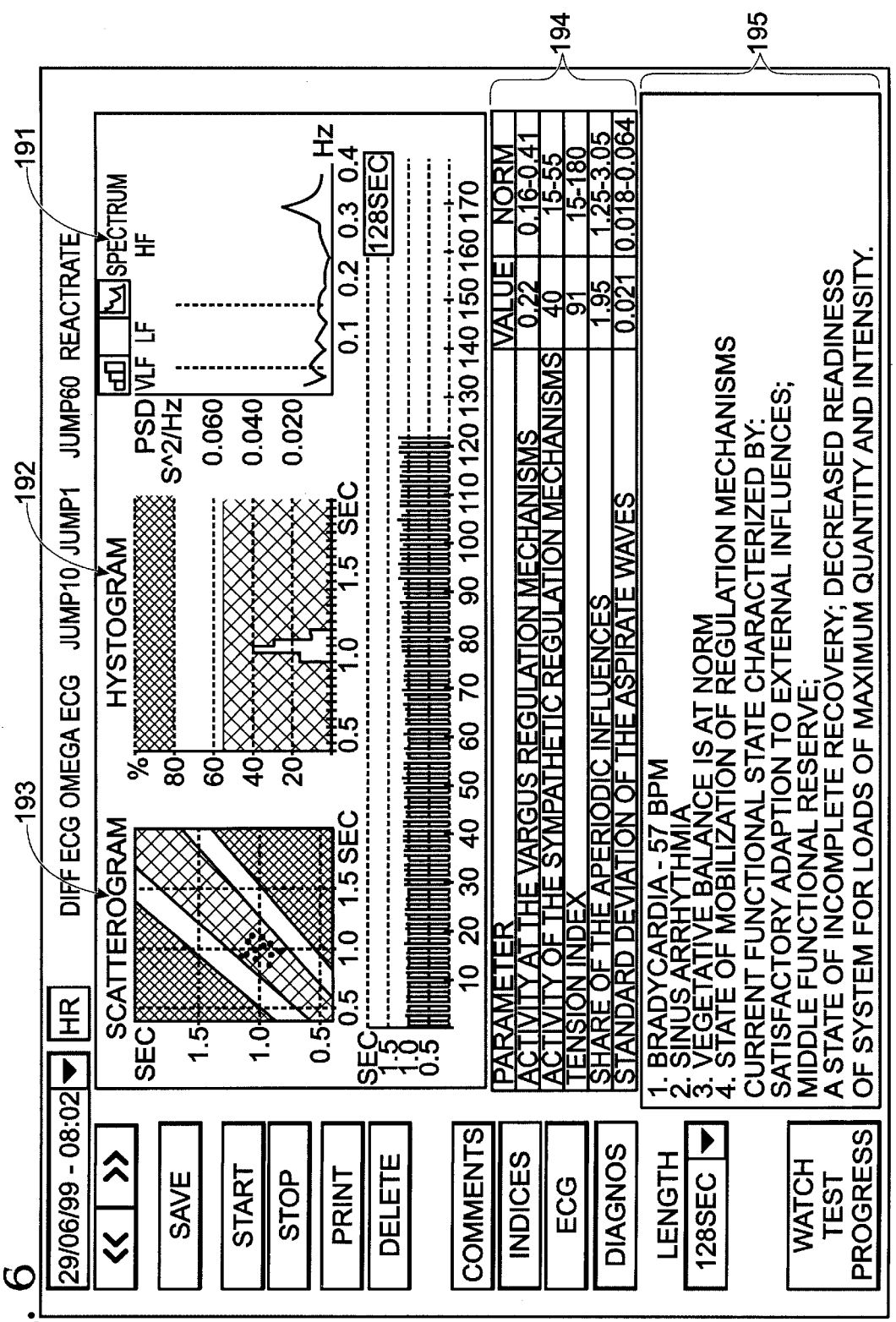
FIG. 6 illustrates a display of data generated in the HRV test of FIG. 5 in accordance with the present invention.

A representative HRV test is described with reference to FIG. 5, which illustrates a flow diagram of machine executing steps for a HRV test in accordance with the present invention. The steps of FIG. 5 and those of the other tests described herein are preferably achieved with application software executing on the processor of CD 50 or via execution of machine executable steps using other current or future developed technology. FIG. 6 illustrate a representative display of HRV test results that preferably includes a cardiogram, the above-mentioned charts/grams and textual conclusions of functional state.

In this representative HRV test, four electrode sensors are preferably utilized and they are preferably placed one each on the wrists and ankles. One sensor electrode is a ground and the other three collect standard ECG data or the like. Alternative sensor placement may be utilized. The HRV test is based on the registration of cardiac contractions of standard electrocardiogram (ECG) readings over the course of a fixed span of time. The test records the change of period length (in seconds) between each cardiac contraction which is the time between ECG spikes, which are designated with the letter R.

After initialization of ID 40, cardiac muscle electrical activity is recorded for a fixed time period, e.g., 128 seconds (step 152). A fixed number of consecutive heart beat intervals (RR intervals), e.g., 100, is selected and analyzed (step 154). The intervals are processed in this preferred method using a fast fourrier transformation to achieve frequency spectrum analysis (step 156) and the density of interval frequencies is plotted in a frequency spectrum-gram 191 (step 158, see FIG. 6). Frequency spectrum analysis is known in the art. The following frequency ranges are preferably plotted: high frequency=0.15 to 0.4 Hz; low frequency=0.04 to 0.15 Hz; and very low frequency=0.004 to 0.04 Hz. A histogram 192 and a scattergram 193 are also preferably generated and displayed (step 160).

In steps 172, various preferred indices for cardio system performance are respectively calculated based on frequency spectrum and other data and these include:

Vagus (parasympathetic) Regulation (VR);

Humoral Regulation (HR);

Sympathetic Regulation (SR);

Stress Index;

Share of aperiodic influences;

Standard deviation; and

Frequency of Cardiac Contractions (FCC).

Calculation of these or related indices is known in the art. (See Baevskiy, R. M., et al., *Mathematical Analysis of Changes in Heart Rate Rhythm Under Stress*, Moscow Science, 1984).

These indices (194) are interpreted (step 191) and preferably compared to a norm (in magnitude and direction) to generate (step 182) textual conclusions about the functional state of cardiac activity. This is preferably done with a rules-based analysis discussed below. Condition statements are preferably generated for at least:

1. type of rhythm;
2. type of regulation of rhythm; and
3. type of vegetative homeostasis.

The type of rhythm is the heart beat rate (in beats per minute, bpm). Type of regulation is based on VR (related to a norm)

and conclusions may include sinus arrythmia (which is normal), stable rhythm, pace-maker dysfunction, etc. Type of vegetative homeostasis is based on HR, VR, and SR and reflects an evaluation of the balance between parasympathetic and sympathetic regulation of the heart. The indices may also be used to generate other conclusions about the functional state of the cardiac system (item 4 in textual conclusion block 195) including degree of stress of the regulatory mechanism (from normal to state of dysfunction), reserve status (from high to very low), readiness of system for loads (from optional to severe cardiac dysfunction demanding immediate cardiology consultation) and adaptation to external influences (from stable to breakdown in adaptation).

The textual conclusion are depicted with reference number 195 in FIG. 6.

Differential ECG (DECG) Test—Metabolism

The heart is a cardiac muscle and energy metabolism in the heart can be monitored with an ECG. Since there is a known correlation between energy metabolism in cardiac muscles and in skeletal muscles, conclusions about the state of skeletal muscles can be drawn from analysis of cardiac muscle energy metabolism.

A representative DECG test is described with reference to FIG. 7, which illustrates a flow diagram of machine executing steps for a DECO test in accordance with the present invention. It should be recognized that various DECG tests may be utilized without departing from the present invention. FIG. 8 illustrates a representative display of DECG test results that preferably includes calculated indices, norm indices and textual conclusions of the functional state of the metabolic system.

To perform a representative DECG test, seven electrode sensors 21–27 are preferably utilized. These include the four electrodes used in the HRV test 21–24 and three more electrodes 25–27 that are placed on the chest in a standard ECG arrangement, though electrode 26 is preferably placed on the right side of the chest.

In step 201, ID 40 is initialized and ECG data is recorded from each sensor for a predefined time period, e.g., 120 seconds. The received ECG signals from the chest sensor electrodes are preferably differentiated (step 203) and analyzed (step 205). A subset, e.g., 10–60 (30 in the present example), of consecutive QRS complexes (peak and recovery of differentiated heart beat contraction) are analyzed and R and S values are ascertained (step 207).

In steps 210, indices for the representative DECG test are generated from the sensed data (preferably including averaged R and S values). These indices include the anaerobic power index (API) which is the magnitude of maximum oxygen consumption, VO2 max, the alactic capacity index (ALCI), the lactic capacity index (LCI), the anaerobic capacity index (ACI), the aerobic efficiency index (AEI), and the system adaptation index (SAI). Calculation of these or related indices is known in the art. (See publications of Kiev Sports Medicine University by Beregovog, V. Y., or Dushanin, S. A. (1986)).

These indices are then analyzed (step 220) to generate textual conclusions about the functional state of the metabolic system. This analysis is preferably carried out using a rules-based analysis as discussed below. The generated condition statements preferably address:

1. state of functional reserves;
2. speed of recovery process;
3. resistance to hypoxia (oxygen debt); and
4. aerobic reserves.

Each of these items way range from high to low and the generated textual conclusions preferably state the corresponding level as shown in textual conclusion block 235.

The calculated indices, norms and textual conclusion are depicted in FIG. 8 with reference numerals 230 and 235, respectively.

Omega Wave (OW) Test—Circulatory, Detox, Hormonal, CN

Omega brain waves and omega brain wave potential (an electrical measurement of omega brain wave magnitude) have been shown to have a relationship to the performance of the central nervous, circulatory, detoxification and hormonal systems.

The following is a representative omega wave (OW) test. It should be recognized that other or related tests that differ from the specific protocol recited below are also within the present invention.

A representative test is described with reference to FIG. 9, which illustrates a flow diagram of machine executable steps for an OW test in accordance with the present invention. FIG. 10 illustrates a display of OW test results that preferably includes charts of resting omega potential v. time (330) and post-load omega potential v. time (335). The textual conclusions of functional state are shown in part in FIG. 11.

The base omega potential at rest has been identified as an indicator of the level of the functional state of the central nervous system and its adaptive reserves. Three levels of base omega potential have been empirically differentiated in healthy people and these are low level (<0 mV), medium level (0–40 mV), and high level (41–60 mV). Low level is characterized by a lowered level of wakefulness, quick exhaustion of psychic and physical functions, unstable adaptive reactions and limited adaptive potential. Medium level is characterized by an optimal level of wakefulness, high stability of psychic and physical functions, sufficient adaptive potential and stable adaptive reactions. High level is characterized by a state of psychic-emotional tension, high stability in response to loads and adequate adaptive reactions.

Iberal and McCullock have shown in their research that there is a time scale for turning on various system resources in response to a stress (i.e., post-load potential). Empirical data has shown that the dynamics of omega potential after an external stress are closely related to the dynamics of various body system processes being turned on. As a result, three time zones of omega potential change, after a single stress load, have been identified and they are Zone A (0–1.5 minutes), Zone B (1.5–4 minutes), and Zone C (4–7 minutes). Zone A characterizes the functional state of the cardio-respiratory (circulatory) system. Zone B characterizes the functional state of the detoxification system (i.e. gastro-intestinal tract, liver and kidneys, etc.). Zone C characterizes the functional state of the hypothalmic, hypophysial and adrenal glands (hormonal system).

The omega wave test is preferably conducted with chlorine-silver weak-isolating electrodes. The electrodes are placed on the test subject (one at the center of the test subject's forehead and one at the base of the right thumb) while the test subject is either sitting or lying in a state of rest.

In step 301, processing logic on CD 50 generates a test start signal and initiates receipt of sensed omega wave potential from ID 40. These signals are preferably recorded for a pre-defined time period (step 303), preferably approximately seven minutes, after which a test end signal is generated. Plot 330, generated in step 305, illustrates a representative plot of this data. The base potential provides a base line from which to access post-load potential.

To perform the post-load assessment, a start signal is generated by CD 50 (step 307) and the PRT undertakes a physical load such as one or two rapid knee bends. The omega potential of the PRT is recorded for a fixed period of time (step 309), approximately seven minutes, after which an end test signal is generated. A graphic representation of the results of the post-load test is preferably generated and plotted as plot 335 (step 313).

The base and post-load potentials are then compared (step 315) in each zone and textual conclusions (step 317) are generated based on the percent difference between the base and post-load potentials, consistent with the chart of FIG. 11. The textual conclusions are preferably generated with a rules-based analysis as discussed below.

In Zone A (circulation), the textual results preferably indicate a state ranging from significant hyperfunction to normal to significant hypofuntion.

In Zone B (detoxification), the textual results preferably indicate a state ranging from normal function to markedly overloaded.

In Zone C (hormonal-adrenal), the textual results preferably indicate a state ranging from significant hyperfunction to normal to significant hypofuntion.

With respect to the central nervous system (CNS), textual conclusions, based on the measured base omega potentials (discussed above) are also preferably generated. These include conclusions that address the state of adaptive reaction of the CNS (ranging from adequate to a restriction in the effectiveness and quality of the adaptation reaction), resistance of CNS to physical and psychic loads (ranging from satisfactory to low resistance) and level of activity of CNS (ranging from optimal to low).

Jump Test—Neuro-Muscular

Referring to FIG. 12, a flow diagram of machine executable steps for a representative jump test in accordance with the present invention is shown.

The following is a representative jump test. It should be recognized that other jump or related tests that differ from the specific protocol recited below are also within the present invention.

The jump test preferably includes one or more of the several component jump tests. The component jump tests preferably include a single series, a ten second and sixty second jump test.

In the single series test, CD 50 prompts a PRT to jump a fixed number of times, e.g. five (step 351). A jump is completed before a signal for the next jump is issued. Time of flight is measured (step 353) to calculate jump height (step 355). Averaged values are preferably calculated. This test measures readiness for explosive efforts and generates appropriate textual conclusions (step 359) based on performance (from high readiness to low readiness).

The ten second jump test is designed to monitor speed and power potential in the alactic regime. CD 50 generates a start signal (step 361) and a PRT jumps as high and as often as he or she can in ten seconds. Number of jumps, time in air, i.e. height, and time on contact surface (which represents rest or readjustment) are measured (step 363). These parameters are essentially indices and they are interpreted to generate the textual conclusions stated below.

The sixty second test is similar, but lasts for sixty seconds. It is designed to monitor speed and power potential in the lactic regime.

Textual conclusions for the ten second test include speed and power in the alactic regime (from high specific power to low specific power) and share of speed and power components (from dominance of speed to shared to dominance of power).

Textual conclusions for the sixty second test include speed and power potential in the lactic regime (from high specific power to low specific power) and speed-power-endurance (from high to low).

The textual conclusions are preferably generated with a rules-based analysis of jump test data.

Stimulus Response (SR) Test—Central Nervous System (CN)

Referring to FIG. 13, a flow diagram of machine executable steps for a representative stimulus response test in accordance with the present invention is shown.

The following is a representative stimulus response test. It should be recognized that other or related tests that differ from the specific protocol recited below are also within the present invention. It should also be recognized that while sound is used as the stimulus in the test below, other sensory signals may be used such as those based on light, visual cues, mechanical or tactile sensation, etc.

The SR test monitors the functional state of the central nervous system and, more specifically, reaction capabilities. The test preferably consists of a series of sounds generated in a fixed time period to which a PRT has to respond.

CD 50 generates a test start signal (step 381) and then randomly generates fifty sounds in a one minute period (step 383). The PRT presses button 38 (FIG. 1) in response to each sound. The delay in response is measured for each sound (step 385). This data is processed to determine the speed and consistency of response (step 387). Mistakes such as pressing the button too soon (anticipating the sound) or too late (loss of concentration) are also recorded.

These parameters or indices are then analyzed (389) to generate textual conclusions that preferably concern:

1. ability of the CN to respond;
2. stability of the neurological processes that determine reaction rate; and
3. reaction rate.

Each of these items is preferably indicated as ranging from high to low. The textual conclusions are preferably generated with a rules-based analysis of stimulus response data.

Rules-Based Analysis

Each of the above tests preferably incorporates a rules-based analysis to interpret indices, graphs and/or other sensed data and to then generate therefrom textual conclusions indicative of functional state of a PRT. The rules-based analysis preferably includes at least a first part and a second part, which are shown diagrammatically in FIG. 14.

In a first part (step 401), the values of relevant indices, parameters or omega potential differences, etc. (depending on the test), are examined and classified for each desired conclusion category or type, e.g., state of functional reserves, in the DECG test. The classification may be based on where a value lies in a range of values calculated from a wider population, or relative to another parameter/index detected during a test (e.g., parasympathetic and sympathetic indices, or base and post-load omega potentials, etc.), or based on an absolute value or compared to some other appropriate standard, etc. The classification may also be dependent on the interaction of multiple indices and/or other information.

In a second part (step 405), the initial classification is re-analyzed and refined, if necessary, e.g., if it falls within a certain distance of another classification or if there is conflicting information, etc. This refinement may include looking at another parameter/index when a value is near the border between two different classifications or reclassifying a value due to a significant deviant value of another related parameter/index, or to compensate for an outlier, etc. A change in classification based on refinement will likely lead to a change in textual conclusion. Various rules-based algorithms are known in the art and these could be modified by a skilled practitioner to implement the criteria set forth above for the listed tests.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features herein before set forth, and as fall within the scope of the invention and the limits of the appended claims.

What is claimed is:

1. An apparatus for assessing the functional state and state of homeostasis in a human, comprising:
   a sensed signal input;
   processing logic coupled to said sensed signal input that performs two or more functional state tests from the group of tests including:
   heart rate variability test;
   differential ECG test;
   brain wave test;
   jump test; and
   stimulus response test;
   said processing logic being configured to receive sensed signals for a given test from said input and to process those signals in such a manner as to produce a signal for that given test that is representative of a textual conclusion of the functional state of a body system which that given test is designed to assess.

2. The apparatus of claim 1, wherein said signal representative of said textual conclusion is generated from a rules-based analysis of sensed data as processed by said processing logic.

3. The apparatus of claim 1, wherein said processing logic is configured to calculate one or more indices values for a given test and to interpret said one or more indices values to generate the signal representative of the textual conclusion that corresponds to that given test.

4. The apparatus of claim 1, further comprising select logic that permits a user to select which of said two or more tests said processing logic is to perform.

5. The apparatus of claim 1, further comprising a mechanism that non-invasively measures physical parameters of a person under test that correspond to said two or more functional tests.

6. The apparatus of claim 1, wherein said processing logic performs three or more of said functional tests.

7. The apparatus of claim 1, wherein said processing logic performs four or more of said functional tests.

8. A method of assessing the functional state of a human, comprising the steps of:
   inputting sensed signals;
   conducting via machine executable steps a first test based on cardiac generated sensed signals to assess the functional state of a first body system;
   conducting via machine executable steps a second test based on brain wave sensed signals to assess the functional state of a second body system different from said first body system;
   generating a first final test output signal that is representative of results of said first test; and
   generating a second final test output signal, separate from said first signal, that is representative of results of said second test.

9. The method of claim 8, further comprising the steps of:
   generating indices from said cardiac generated sensed signals or said brain wave sensed signals; and
   interpreting said generated indices to create a signal representative of a textual conclusion about the functional state of a body system corresponding to said indices.

10. The method of claim 9, wherein said interpreting step includes the step of using a rules-based analysis to carry out said interpretation.

11. The apparatus of claim 3, wherein said processing logic is further configured to compare said calculated index value to a norm index value in generation of said signal representative of the textual conclusion.

12. The apparatus of claim 1, wherein said processing logic is further configured to process received sensed signals in such a manner as to produce for a given test a signal that is representative of a graphical depiction of results of that test.

13. The apparatus of claim 1, wherein said processing logic is further configured to produce said representative signal such that said signal is indicative of an indirect assessment of the functional state of a body system.

14. The apparatus of claim 11, wherein the comparison performed by said processing logic determines the direction and magnitude of said calculated index value from said norm index value and generates the signal representative of textual conclusion based on the determined direction and magnitude.

15. The method of claim 8, further comprising the steps of:
   generating indices from said cardiac generated sensed signals or said brain wave sensed signals; and
   comparing said generated indices to norm indices values.

16. The method of claim 8, wherein said step of conducting a first test based on cardiac generated sensed signals includes the step of conducting an electro-cardiogram test.

17. The method of claim 8, wherein said step of conducting a first test based on cardiac generated sensed signals includes the step of conducting a heart rate variability test.

18. The method of claim 8, further comprising the step of conducting via machine executable steps a third test to assess the functional state of a third body system different from said first and said second body systems.

19. An apparatus for assessing the functional state of a human, comprising:
   a sensed signal input;
   cardiac signal processing logic that conducts a first test based on sensed cardiac signals to assess the functional state of a body system;
   brain signal processing logic that conducts a second test based on sensed brain wave signals to assess the functional state of a body system; and
   logic that generates index values from said cardiac generated sensed signals or said brain wave sensed signals and interprets said generated index values to create a signal representative of a textual conclusion concerning the functional state of a body system corresponding to said index values.

20. The apparatus of claim 19, wherein said logic compares generated index values to a norm and creates said representative signal said comparison.

21. The apparatus of claim 19, wherein said first test is an electro-cardiogram test.

22. The apparatus of claim 19, wherein said first test is a heart rate variability test.

23. The apparatus of claim 19, wherein said sensed brain wave signals are omega wave signals.

24. An apparatus for assessing the functional state of a human, comprising:

a sensed signal input;

cardiac signal processing logic that conducts a first test based on sensed cardiac signals to assess the functional state of a body system;

brain signal processing logic that conducts a second test based on sensed brain omega wave signals to assess the functional state of a body system.

25. The apparatus of claim 24, wherein said first test is an electro-cardiogram test.

26. The apparatus of claim 24, wherein said first test is a heart rate variability test.

27. The apparatus of claim 24, wherein at least one of said cardiac logic and said brain logic generates a signal representative of a textual conclusion concerning the functional state of a corresponding body system.

28. An apparatus for assessing the functional state of a human, comprising:

a sensed signal input;

cardiac signal processing logic that conducts a first functional state test based on sensed cardiac signals and generates a first value representative of the result of said first test; and brain signal processing logic that conducts a second functional state test based on sensed brain wave signals and generates a second value representative of the results of said second test;

comparison logic that compares at least one of said first and second generated test values to a norm value and generates a test output signal based on said comparison that is representative of an indirect assessment of a body system.

29. The apparatus of claim 28, wherein said second functional state test is based on omega wave brain signals.

30. The apparatus of claim 28, wherein said generated signal is representative of a textual conclusion concerning said indirect assessment of a body system.

* * * * *